(12) United States Patent  
Hou et al.

(10) Patent No.: US 9,335,294 B2  
(45) Date of Patent: May 10, 2016

(54) TEST STRIP AND METHOD FOR HUMIDITY DETECTION

(71) Applicant: TAIDOC TECHNOLOGY CORPORATION, New Taipei (TW)

(72) Inventors: Hui-Sheng Hou, New Taipei (TW); Chia-Chi Wu, New Taipei (TW); Tai-Cheng Chou, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 469 days.

(21) Appl. No.: 13/869,000

(22) Filed: Apr. 23, 2013

(65) Prior Publication Data

US 2013/0292264 A1    Nov. 7, 2013

(30) Foreign Application Priority Data

May 2, 2012  (TW) .............................. 101115689 A

(51) Int. Cl.
- G01N 27/327  (2006.01)
- G01N 27/416  (2006.01)
- G01N 27/22  (2006.01)
- G01N 27/12  (2006.01)
- G01N 27/60  (2006.01)
- G01N 27/02  (2006.01)

(52) U.S. Cl.
CPC .......... *G01N 27/4163* (2013.01); *G01N 27/121* (2013.01); *G01N 27/223* (2013.01); *G01N 27/3272* (2013.01); *G01N 27/3274* (2013.01); *G01N 27/02* (2013.01); *G01N 27/605* (2013.01); *G01N 2201/1214* (2013.01); *G01N 2291/02845* (2013.01)

(58) Field of Classification Search
CPC .......... G01N 21/81; G01N 2201/1214; G01N 2291/02845; G01N 21/76; G01N 21/763; G01N 2021/7759; G01N 27/223; G01N 27/605; G01N 27/02; G01N 27/3272; G01N 27/3274
See application file for complete search history.

(56) References Cited

U.S. PATENT DOCUMENTS

| | | | | |
|---|---|---|---|---|
| 6,046,058 A * | 4/2000 | Sun | ..................... | G01N 33/5302 422/412 |
| 2008/0254441 A1 * | 10/2008 | Mohammed | ......... | G01N 33/558 435/5 |
| 2013/0002278 A1 * | 1/2013 | Martin | ................. | G01N 27/048 324/750.3 |

* cited by examiner

*Primary Examiner* — Alexander Noguerola

(74) *Attorney, Agent, or Firm* — Chun-Ming Shih

(57) ABSTRACT

The present invention related to a test strip and a method for humidity detection. The test strip comprises two humidity detecting materials for detecting humidity change and one of the humidity detecting materials is exposed to outer environment. Detect the two humidity changes to obtain a ratio that is used for comparing with a value and then it can prevent from exceeding a predetermined humidity value, and whereby the test strip and the method could achieve the goal of simple humidity detection.

20 Claims, 10 Drawing Sheets

TEST STRIP AND METHOD FOR HUMIDITY DETECTION

BACKGROUND OF THE INVENTION

1. Field of the Invention

The present invention relates in general to a test strip and a method for humidity detection, and particularly relates to a test strip and a method for humidity detection by detecting a ratio of detected value of two humidity detecting materials.

2. Description of the Related Art

Since the progress of science and technology and the change of life style, many tests operated in hospital from the past may be operated at home now. The increasing patient number of chronic disease is especially related with the lifestyle change so as to accelerate the industry development for home diagnosis, and the test items preferred to perform at home include blood glucose, ovulation and pregnancy diagnosis.

In market, many types of disposable biosensor strip are suitable for nonprofessional users and can be operated at home without contamination issue, and in coordinated with the mating biosensing meter to obtain the measuring value.

In addition, conventional lateral flow test strip on clinic diagnosis is used for analyzing an analyte present in the sample such as body fluid. For example, the lateral flow test strip adapted for determining hCG (human chorionic gonadotropin) has been widely commercialized.

The packaging type of conventional test strip described above has multi-strips packaging or single-strip packaging. The multi-strips packaging is storing about ten to fifty strips into a desiccant container, and users took out the desired number of strips from the desiccant container. Opening the desiccant container repetitively will change the humidity inside of the desiccant container so as to affect the humidity condition of test strips. The test strip includes a reagent interactive with an analyte, and the humidity change may affect the reagent to interfere with the test result. Even the single-strip packaging still may package improperly to cause humidity change.

Therefore, there is an issue for manufacturer that how to make sure the humidity of pre-use test strip is within a normal range so as to need further improvement about deficiency described above for manufacturer.

SUMMARY OF THE INVENTION

According to one aspect of the present invention is to provide a test strip for humidity detection, comprising a base, a detecting element, two humidity detecting materials and a cover. The detecting element is disposed on the base. The two humidity detecting materials are respectively disposed on the detecting element. The cover is disposed upon the detecting element and the base, and to let one of the humidity detecting materials expose to outer environment.

In an embodiment in accordance with the present invention, the detecting element has a humidity sensing trace near one end of the test strip, and the humidity sensing trace comprises a first humidity sensing area and a second humidity sensing area, and the two humidity detecting materials are respectively disposed on the first humidity sensing area and the second humidity sensing area. Preferably, the humidity sensing trace is comb-shaped.

In an embodiment in accordance with the present invention, the detecting element is an electrode system comprising at least one contact pad, at least one electrode and at least one conducting trace disposed between the contact pad and the electrode, and the contact pad and the electrode are disposed on different side, and the humidity detecting materials are impedance property of humidity detecting material. Preferably, the first humidity sensing area and the second humidity sensing area respectively comprises two electrodes, and the electrodes are respectively connected with different contact pads. Preferably, the first humidity sensing area and the second humidity sensing area are shared with one of the electrodes or the conducting traces.

In an embodiment in accordance with the present invention, the electrode system is consisted of a silver layer and a carbon layer, and the electrode surface of the silver layer is larger than that of the carbon layer in the humidity sensing area.

In an embodiment in accordance with the present invention, the contact pad contacted with a mating test device is used for detecting an impedance value of the humidity sensing area.

In an embodiment in accordance with the present invention, the cover further comprises a hole, and the hole is located corresponding to one of the humidity detecting materials to let it in an exposed state, and the other one of the humidity detecting materials is in an unexposed state.

In an embodiment in accordance with the present invention, one of the humidity sensing areas is disposed near lateral edge and the cover is cooperated with the base to formed a notch on the lateral edge corresponding to the one of the humidity sensing areas to let the one of the humidity sensing areas expose to outer environment.

In an embodiment in accordance with the present invention, the test strip further comprises an isolating layer disposed between the cover and the detecting element, and exposed at least one end of the detecting element to form a space between the cover and the base, and the isolating layer comprising an opening notch corresponding to the lateral edge of humidity sensing areas.

In an embodiment in accordance with the present invention, the test strip is electrochemical biosensor strip used for determining concentration of an analyte, and the test strip further comprises a reaction area used for determining the analyte concentration.

In another aspect in accordance with the present invention, the present invention provides a test strip for humidity detection, comprising a reaction area and a casing. The reaction area comprises two humidity sensing traces, and the two humidity sensing traces respectively comprise a humidity detecting material. The casing covers the reaction area, and to let one of the humidity detecting materials exposed to outer environment.

In an embodiment in accordance with the present invention, the casing further comprises an opening to let the one of the humidity detecting materials exposed to outer environment.

In an embodiment in accordance with the present invention, the test strip further comprises a sample introducing area used for receiving a sample. The reaction area is receiving the sample from the sample introducing area, and further comprises a test line used for combining with an analyte.

In one another aspect in accordance with the present invention, the present invention provides a method for humidity detection, comprising inserting a test strip into a test device, wherein the test strip comprising a first humidity sensing area and a second humidity sensing area. Besides, detect a detected value R1 of the first humidity sensing area and a detected vale R2 of the second humidity sensing area. Further, calculate a ratio value of the detected value R1 and the detected value R2. Additionally, compare the ratio value to a predetermined value to obtain a result.

In an embodiment in accordance with the present invention, the detected value is resistance value, capacitance value or inductance value.

In an embodiment in accordance with the present invention, the method further comprises showing an error message or a measuring message when the ratio value higher or lower than the predetermined value.

In an embodiment in accordance with the present invention, one of the humidity sensing areas in the test strip is in an exposed state, and the other one of the humidity sensing areas is in an unexposed state.

In an embodiment in accordance with the present invention, the method of the step after calculating the ratio value of the detected value R1 and the detected value R2 further comprises saving the ratio value. Besides, measure an analyte concentration to obtain a measured value. Further, compare the ratio value to a correcting table. Additionally, corrects the measured value by the correcting table to obtain a corrected concentration.

According to the aspect of the present invention as description above, the test strip and the method in accordance with the present invention is detecting humidity change from two humidity sensing areas to obtain a ratio, and comparing with a predetermined value so as to determine whether the test strip exceeding appropriate humidity value for use, and whereby achieving the goal of improving conventional deficiency.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENTS

Figure 1:
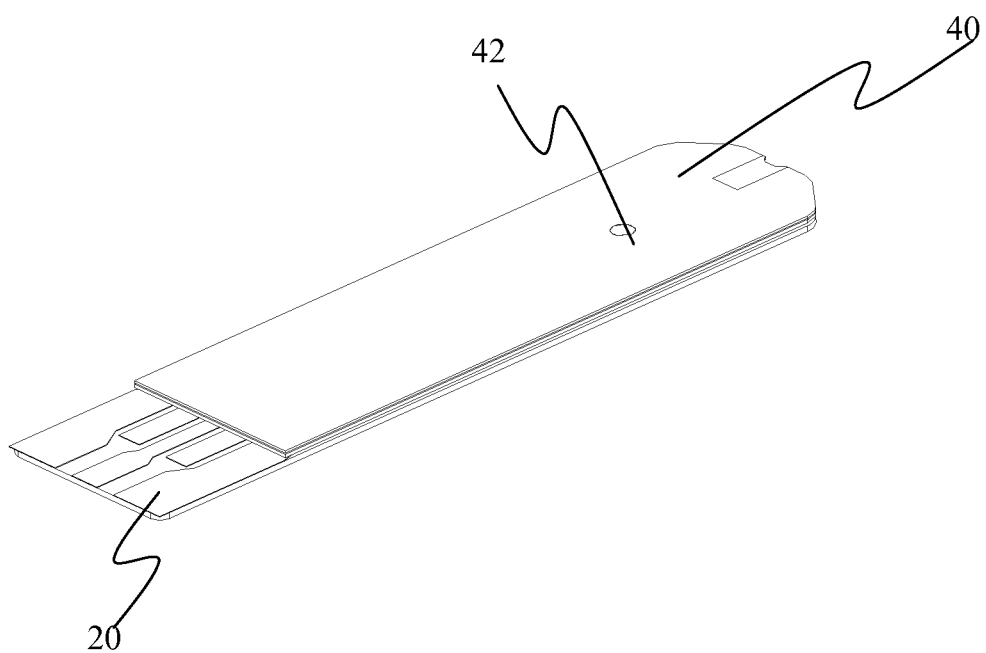
FIG. 1 is a schematic perspective view of a preferred embodiment of a test strip in accordance with the present invention.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. Such alternative embodiments require certain adaptations to the embodiments discussed herein that would be obvious to those skilled in the art.

The following description and accompanying drawings are some examples in accordance with the present invention. The same symbol herein in the drawings indicates the same or similar structure.

The present invention provides a test strip for humidity detection, especially related to detecting a ratio of the change of two or more humidity detected values or calculating values of that so as to determine if the humidity deviating from a predetermined range.

The humidity in accordance with present invention can be absolute humidity or relative humidity. Preferably, the humidity in accordance with the present invention is relative humidity.

Figure 2:
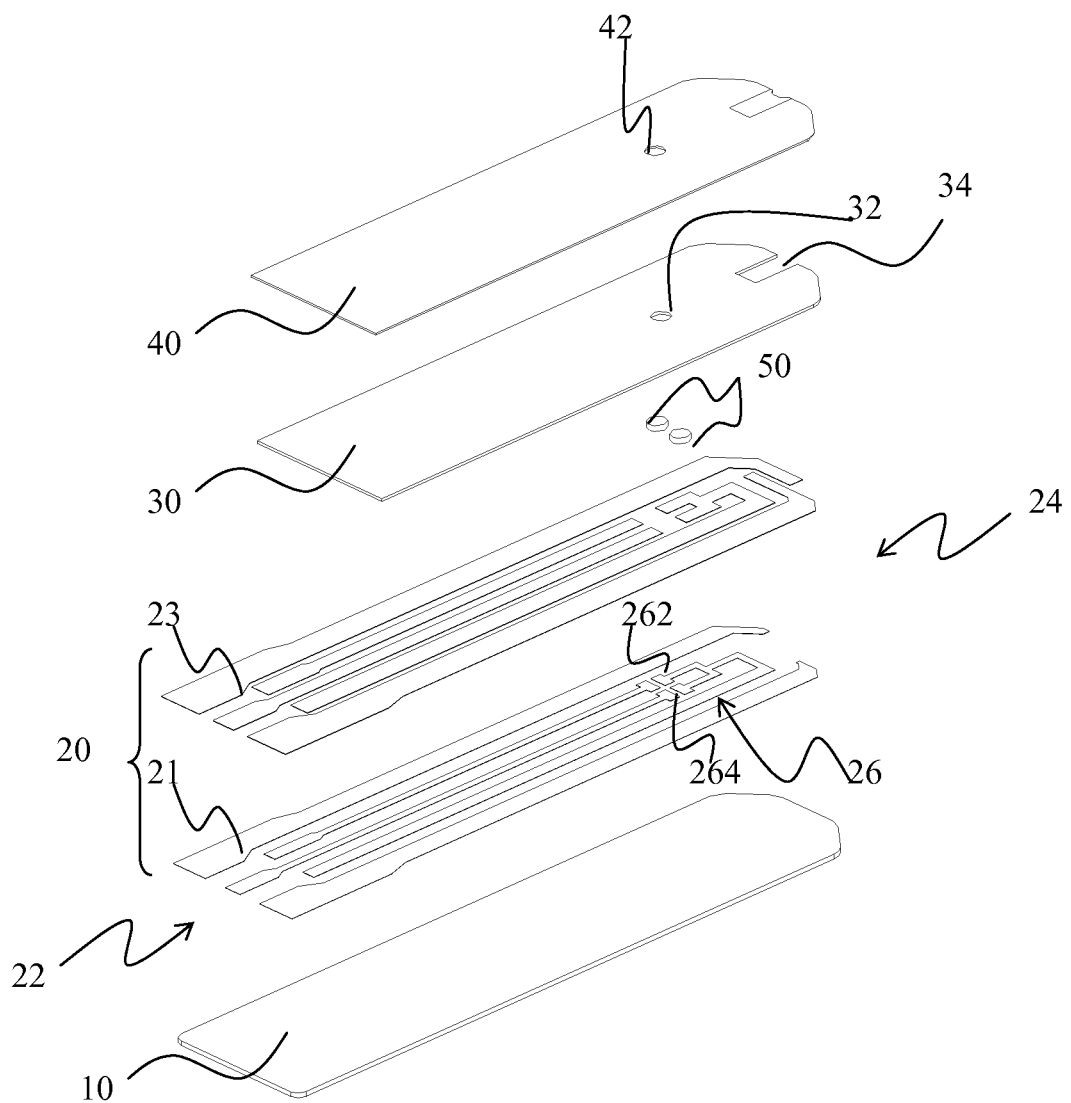
FIG. 2 is an exploded schematic perspective view of the preferred embodiment of the test strip in FIG. 1 in accordance with the present invention.

With reference to FIGS. 1 and 2 in combination, they show a schematic perspective view and an exploded schematic perspective view of a preferred embodiment of a test strip in accordance with the present invention. The test strip comprises a base (10), a detecting element (20), a humidity detecting material (50) and a cover (40).

The base (10) can be an insulating substance and has electrical insulating characteristic. Preferably, the appearance of the base (10) can be square-typed. More preferably, one or more angles of the square-typed base (10) can be obtuse or curved surface to prevent users from harming by sharp angle.

The detecting element (20) is disposed on the base (10), and the way covered on the base (10) can be any conventional way in accordance with prior art, such as screen printing, sputtering coating, evaporating coating and so on. In a preferred embodiment of the present invention, the detecting element (20) comprises a first end (22), a second end (24) and a humidity sensing trace (26). The first end (22) can be one end to be used to contact with a mating test device. The second end (24) is an opposite end corresponding to the first end (22). The humidity sensing trace (26) is disposed between the first end (22) and the second end (24), and comprises a first humidity sensing area (262) and a second humidity sensing area (264).

In an embodiment in accordance with the present invention, the detecting element (20) comprises a contact pad, an electrode and a conducting trace. The contact pad is located on the first end (22), and the electrode is located on the second end (24). The conducting trace is connected between the contact pad and the electrode. The first humidity sensing area (262) and the second humidity sensing area (264) respectively comprise two electrodes. The electrodes are respectively connected with different contact pads so that the contact pad contacted with the mating test device for detecting a value of the humidity sensing areas (262, 264). In an embodiment in accordance with the present invention, the first humidity sensing area (262) and the second humidity sensing area (264) can share with one of the electrodes or the conducting traces.

In other preferred embodiment in accordance with the present invention, the detecting element (20) can be one or more layers. Preferably, the detecting element (20) is a conductive electrode system made by conductive material, and the conductive material is pure material, alloy or mixing with other substances. The conductive material can be, for example, aluminum, copper, carbon, silver, gold, palladium, chromium, titanium, or a mixture described above, but the present invention shall not limited for this. Preferably, the detecting element (20) has two electrode layers such as one can be carbon layer and the other one can be silver layer or one can be copper layer and the other one can be gold layer. Please refer to FIG. 2, the detecting element (20) is a silver layer (21) and a carbon layer (23) for example. In the present embodiment, the detecting element (20) is an electrode conductive system so as to detect the change with impedance value such as resistance value, capacitance value or inductance value for humidity detection.

Please refer to FIG. 2. In an embodiment in accordance with the present invention, the detecting element (20) comprises the silver layer (21) and the carbon layer (23). The humidity sensing trace (26) is consisted of the silver layer (21) and the carbon layer (23), and discriminated to the first humidity sensing area (262) and the second humidity sensing area (264). The humidity sensing areas (262, 264) composed of the silver layer (21) and the carbon layer (23) and are respectively including two electrodes and shared with one of the electrodes. The surface of the two electrodes of the silver layer (21) corresponding to the humidity sensing area is larger than that of the two electrodes of the carbon layer (23).

The humidity detecting material (50) is disposed on the humidity sensing trace (26) of the detecting element (20). The humidity detecting material (50) can be any kind of substance used for humidity detection in the prior art. In the present invention, the humidity detecting material (50) preferably is impedance property of humidity detecting material, but the present invention shall not be limited for this. Those skilled in the art are familiar with the substance used as humidity detecting material (50). Preferably, the humidity detecting material (50) can be the deliquescent salt such as calcium chloride ($CaCl_2$), magnesium chloride ($MgCl_2$), zinc chloride ($ZnCl_2$), and so on. There can be any types and methods used for forming the humidity detecting material (50) on the humidity sensing trace (26). For example, dripping the humidity detecting material (50) on the humidity sensing trace (26) then drying the humidity detecting material (50) to fix on the humidity sensing trace (26), or filming a lamina upon the humidity sensing trace (26), but the present invention shall not be limited for this. For instance, if the humidity detecting material (50) is impedance sensitized, receiving aqueous vapor will change the impedance value of the humidity detecting material for achieving the goal of humidity detection.

In an embodiment in accordance with the present invention, the present invention have two humidity detecting materials, and respectively disposed on the first humidity sensing area (262) and the second humidity sensing area (264). Preferably, the two humidity detecting materials (50) are the same substance.

The cover (40) is disposed upon the detecting element (20). In the present embodiment, the cover (40) is used to expose the first end (22) of the detecting element (20), and preferably the cover (40) is used to expose the contact pad.

Please refer to the embodiment in FIG. 2. The cover (40) further comprises a hole (42). The hole (42) is located corresponding to one of the humidity detecting materials (50) so that two humidity detecting materials (50) are respectively exposed and unexposed to outer environment. In other words, one of the humidity detecting materials (50) is in an unexposed state and the other one of the humidity detecting materials (50) is in an exposed state. Therefore, either the test strip stored in the desiccant container or took out from the desiccant container to expose in air by users, the humidity of the test strip will be detected by the impedance value variation caused by humidity change of the two humidity detecting materials (50) when the test strip contacted with the mating test device. Users will know if the test strip is over an appropriate humidity.

The designed pattern of two humidity detecting materials (50) of the test strip respectively exposed and unexposed to outer environment can be detected a ratio of two detected values such as impedance value to compare with a predetermined value for humidity detection, and thereby preventing the deviation from detecting an absolute value of solo humidity detecting material.

The impedance value has an illustration of a resistance value for instance in following. According to the conventional resistance value calculating formula $R=\rho L/A$, and $\rho$ is a proportionality constant as a resistance coefficient, L is length and A is cross section area. Humidity detected by single resistance value has been affected by deviation of the length or cross section area of detecting element (20) in manufacturing process so that it may be make a mistake for testing the humidity condition. For example, assumed that the relative humidity higher than 85% is indicated an exceeding humidity condition to affect the test result, and detected by solo humidity sensing area may show the resistance value as 10 $K\Omega$ or 15 $K\Omega$ to indicate the same relative humidity value 85% affected by the manufacturing process so that mistaking with the test result.

Therefore, the ratio of two detected values of humidity sensing area to compare with a predetermined value for humidity condition is decreasing the deviation from manufacturing process.

Figure 3A:
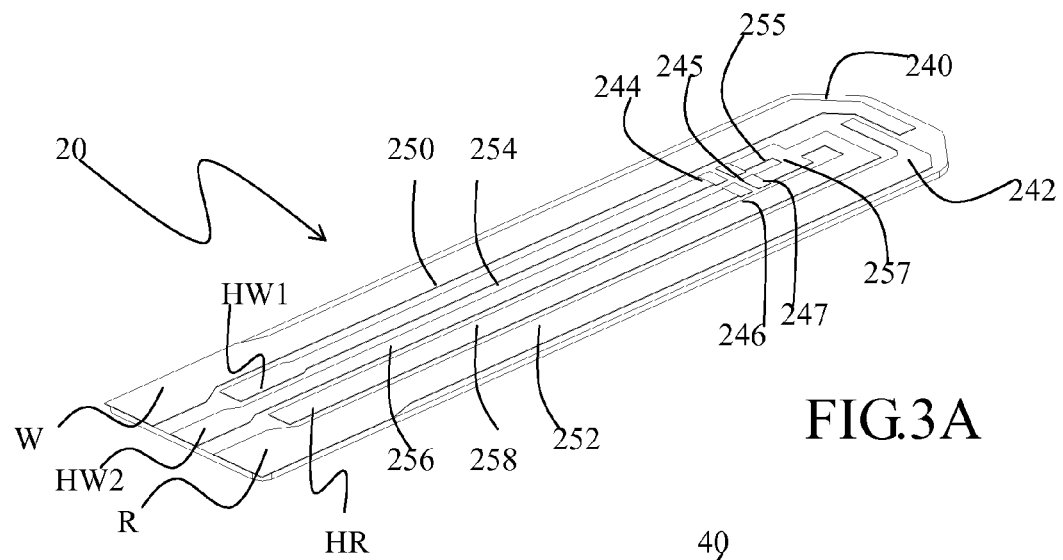
FIG. 3A is a schematic perspective view of a detecting element and a humidity sensing trace of the test strip in FIG. 1 in accordance with the present invention.
Figure 3B:
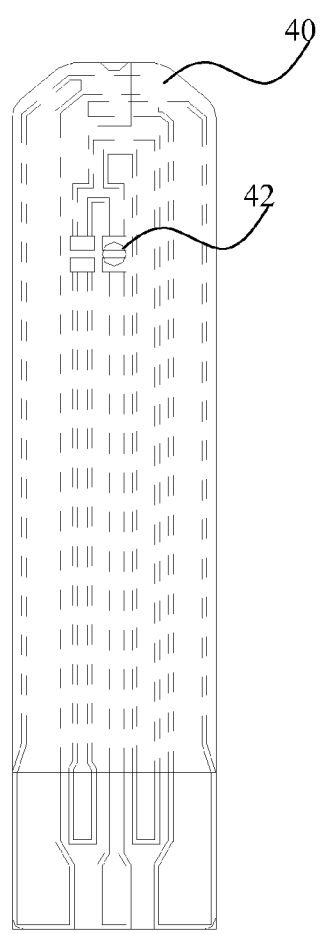
FIG. 3B is a top view of a cover covering on the test strip in FIG. 3A.

Please refer to FIGS. 3A and 3B in combination. FIG. 3A is a preferred embodiment of the detecting element (20), and FIG. 3B is schematic perspective view of a cover (40) covering on the test strip. In FIGS. 3A and 3B, there is apparently a hole (42) located corresponding with one of the humidity sensing areas to let the selected humidity sensing area in an exposed state, and the other one of the humidity sensing areas is in an unexposed state. Preferably, two humidity sensing areas are positioned adjacent with each other in the test strip.

In an embodiment in accordance with the present invention, the test strip further comprises an isolating layer (30) located intermediately between the cover (40) and the detecting element (20). The isolating layer (30) exposed at least one end of the detecting element (20) to form a space between the cover (40) and the base (10). The isolating layer (30) can be an adhesive layer to joint with the cover (40), the base (10) and the detecting element (20). The isolating layer (30) can be insulated material.

In an embodiment in accordance with the present invention, when the cover (40) comprises a hole (42), the isolating layer (30) comprises a notch (32) positioned corresponding to the hole (42) so as to let one of the humidity detecting materials (50) exposed to outer environment.

In other embodiment in accordance with the present invention, the test strip is used for measuring concentration of an analyte, and the isolating layer (30) further comprises a reaction area (34). When the cover (40) assembled with the base (10), the reaction area (34) is formed a capillarity receiving area so as to receive sample containing selective analyte. Preferably, the analyte can be glucose, cholesterol, uric acid and so on, and the sample can be blood, urine, sweat, body fluid and so on. According to different detecting principles of the analyte, the reaction area (34) can be deposited with different kind of the reactive reagent.

For example, the reactive reagent can be biological active materials (such as enzyme), enzyme co-factor, stabilizer (such as high molecular polymer), buffer and so on.

Please refer to FIG. 3A. The second end of detecting element (20) comprises a working electrode (240), a reference electrode (242), a first humidity detecting working electrode (244), a first humidity detecting reference electrode (245), a second humidity detecting working electrode (246) and a second humidity detecting reference electrode (247), and respectively connected with a working electrode conducting trace (250), a reference electrode conducting trace (252), a first humidity detecting working electrode conducting trace (254), a first humidity detecting reference electrode conducting trace (255), a second humidity detecting working electrode conducting trace (256) and a second humidity detected reference electrode conducting trace (257). The first humidity detecting reference electrode conducting trace (255) and the second humidity detecting reference electrode conducting trace (257) are further connected with a common conducting trace (258). The working electrode conducting trace (250), the reference electrode conducting trace (252), the first humidity detecting working electrode conducting trace (254), the second humidity detecting working electrode conducting trace (256) and the common conducting trace (258) are further respectively connected with a contact pad W, a contact pad R, a contact pad HW1, a contact pad HW2 and a contact pad HR.

In the embodiment described above, the common conducting trace is a designed pattern used for reducing distribution of the conducting trace, but the present invention shall not be limited for this. The designed pattern also can be the first humidity sensing trace and the second humidity sensing trace shared with a humidity detecting reference electrode which connected with a humidity detecting reference electrode conducting trace.

In a preferable embodiment, the test strip in accordance with the present invention is used for determining blood glucose. The way of storing test strip is putting a plurality of test strips into a desiccant container, and then opening the desiccant container to take out desired number of the test strips for use. Therefore, either how long the test strip stored in the desiccant container or took out from the desiccant container to expose in air, it can detect a ratio value of the resistant value of two humidity sensing areas to compare with a predetermined value so as to determine whether the test strip having appropriate humidity condition for testing. On the other hand, the ratio values can be corresponding to corrected values to correct the blood glucose value in different humidity then showing the corrected blood glucose value. Following has more detail description.

In accordance with the present invention, the detecting element can be designed with different pattern. FIG. 3 is a preferable embodiment, and the following has illustration with different pattern for instance, but the present invention shall not be limited for this.

Figure 4A:
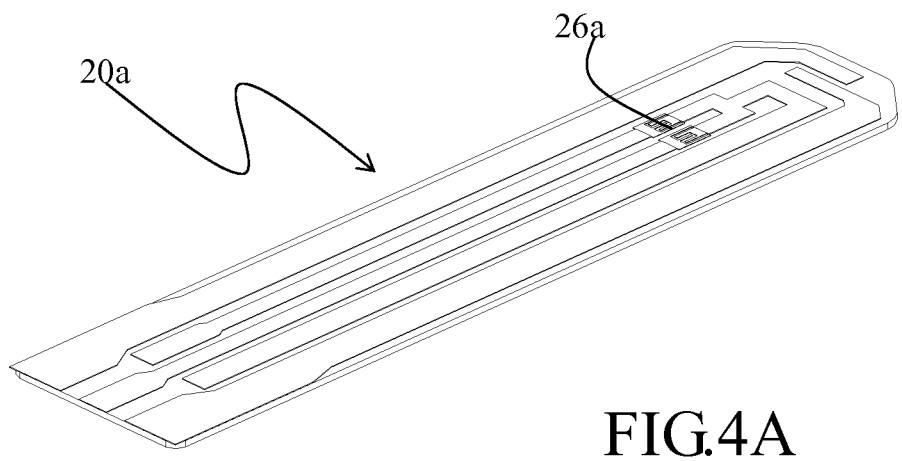
FIG. 4A is a schematic perspective view of a second preferred embodiment of the detecting element and the humidity sensing trace of the test strip in accordance with the present invention.
Figure 4B:
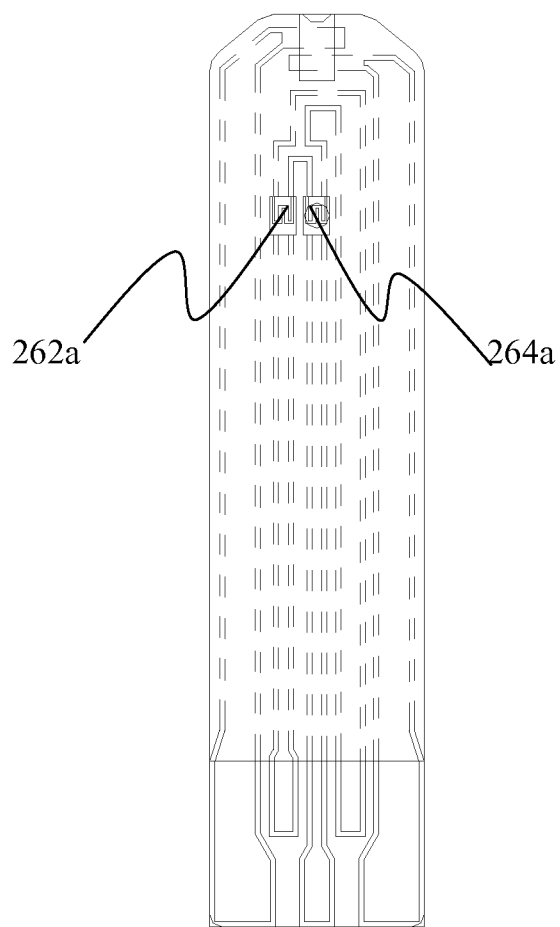
FIG. 4B is a top view of a cover covering on the test strip in FIG. 4A.

Please refer to FIGS. 4A and 4B in combination. They show a second preferred embodiment of a schematic perspective view showing the distribution of the detecting element and a schematic perspective view showing the cover covering on the test strip. As FIG. 4A shown, the designed pattern of a detecting element (20a) is different from that showed in FIG. 3A. A humidity sensing trace (26a) of the detecting element (20a) is comb-shaped for increasing detecting surface and test sensitivity. As shown in FIG. 4B, either the first humidity sensing area (262a) or the second humidity sensing area (264a) is exposed to outer environment.

In order to form one of humidity sensing areas exposed to outer environment and the other one of that unexposed to outer environment, the type of designed pattern is not limited with a hole located on the cover, and it also can design with other types. Please refer to FIGS. 5A to 5D in combination. They show a third embodiment of a schematic perspective view showing the distribution of the detecting element, a schematic perspective view of the cover covering on the test strip, a cross-sectional view of C-C line in FIG. 5B and an exploded schematic perspective view.

Figure 5A:
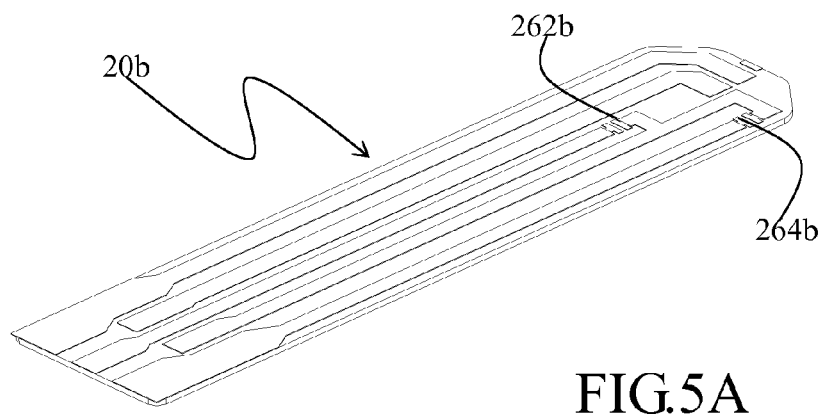
FIG. 5A is a schematic perspective view of a third preferred embodiment of the detecting element and the humidity sensing trace of the test strip in accordance with the present invention.
Figures 5B, 5C:
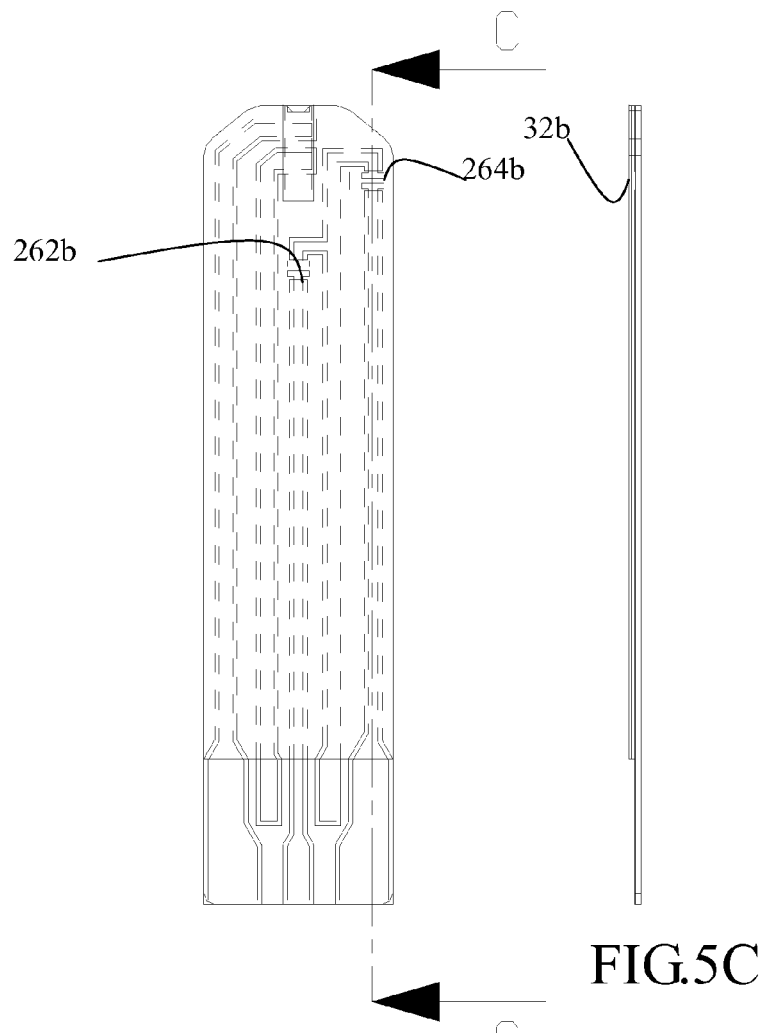
FIG. 5B is a top view of a cover covering on the test strip in FIG. 5A.
FIG. 5C is a cross-sectional view of C-C line in FIG. 5B.
Figure 5D:
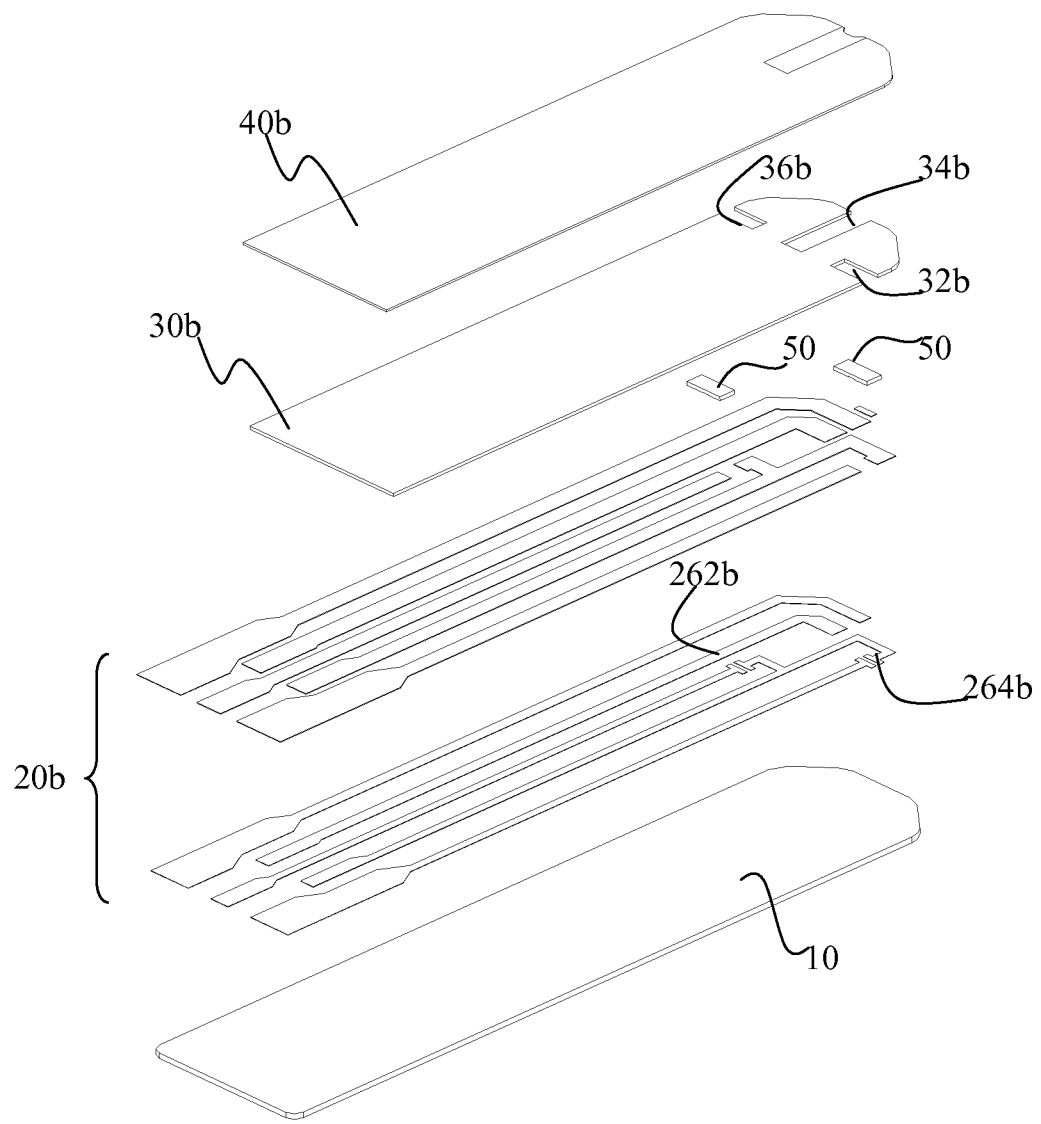
FIG. 5D is an exploded schematic perspective view of the test strip in FIG. 5B.

In an embodiment in accordance with the present invention, the detecting element (20b) has two humidity sensing areas (262b, 264b), and one of the humidity sensing areas (264b) is disposed near lateral edge. The cover (40b) does not comprise a hole but cooperated with the base (10) to form a notch (32b) located in the lateral edge for exposing the humidity sensing area (264b) which is near lateral edge. Therefore, there is one of the humidity sensing areas (264b) exposed to outer environment, and the other one of the humidity sensing areas (262b) is unexposed to outer environment. Preferably, the type of notch (32b) can be formed on the isolating layer (30b), and located corresponding to the humidity sensing area (264b) which is near lateral edge. When the cover (40b) adhered with the isolating layer (30b), the notch (32b) lets the humidity sensing area (264b) expose to outer environment (as shown in FIG. 5C).

Further, the test strip in the present embodiment is used to determine concentration of the analyte. The isolating layer (30b) further comprises a reaction area (34b) as the first embodiment described above. The analyte contained in the sample is passed through the reaction area (34b) to react, and then the detecting element (20) transmitted signal to obtain test result.

The reaction area (34b) received the sample by capillary, and the notch (32b) on the isolating layer (30) can be an air vent to increasing the sample receiving rate. Preferably, the isolating layer (30) is opened a second notch (36b) located opposite side with the notch (32b) to receive the sample equally.

The test strip in the present invention is not only being the electrochemical test strip but also the optical test strip used for test such as pregnancy test, ovulation test, urine test and so on.

Figure 6A:
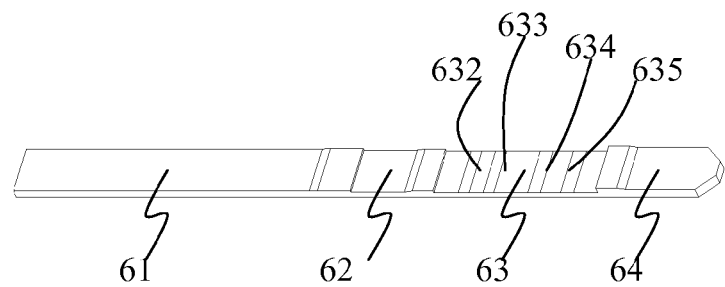
FIG. 6A is a schematic perspective view of a fourth preferred embodiment of the test strip in accordance with the present invention.
Figure 6B:
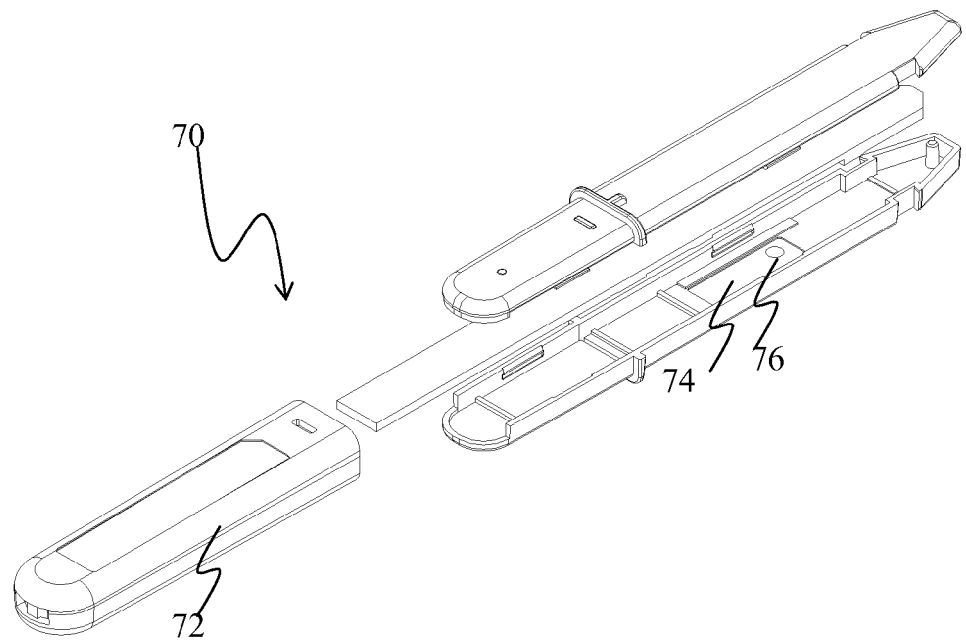
FIG. 6B is an exploded schematic perspective view of a casing assembled with the test strip in FIG. 6A.

Please refer to FIGS. 6A and 6B in combination. They show a fourth embodiment of a schematic perspective view of the test strip and an exploded schematic perspective view of a casing assembled with the test strip in accordance with the present invention.

The test strip comprises a sample introducing area (61) and a reaction area (63). Preferably, the test strip further comprises a reagent area (62) and an absorptive area (64).

The sample introducing area (61) is used for receiving sample contained the analyte. The reaction area (63) preferably comprises a test line (632) and a humidity test line (634). The test line (632) includes a substrate fixing on the reaction area (63) for reacting with the analyte. The humidity test line (634) includes the humidity detecting material, and preferably the color of the humidity detecting material will change by the humidity variation. For example, the humidity detecting material can be deliquescence salt such as calcium chloride ($CaCl_2$), magnesium chloride ($MgCl_2$), zinc chloride ($ZnCl_2$) and so on. Preferably, the humidity test line (634) is positioned downstream from the test line (632). The way to fix humidity detecting material on the reaction area (63) can be any conventional technique in accordance with the prior art. Preferably, the humidity detecting material may contain other substrate assisted to fix on the reaction area (63), or the humidity detecting material fixed on the reaction area (63) is made by other manufacturing technique.

The test strip further comprises a casing (70). The casing (70) covered with the test strip, and has a window (74). The window (74) is located corresponding to the reaction area (63) on the test strip. The casing (70) further comprises a lid (72). Users can take off the lid (72) from the casing (70) to contact with sample by the sample introducing area (61) for using. The sample is received into the test strip by the sample introducing area (61), and then moving toward the reaction area (63) by capillary. The sample contained the analyte can react with the substrate on the test line (632) of the reaction area (63) for showing a result.

The test strip assembled with the casing (70) to cooperate with an electronic analysis device, and the electronic analysis device has a light source and a light detector corresponding to the window (74). The test strip puts into the electronic analysis device for detecting the measurement value of the humidity test line (634) by the light source and the light detector to compare with a predetermined value. If the change of the color of the humidity sensing area (634) accompanied with humidity variation is exceeding the predetermined value, an error message will be showed to indicate that the test strip is improper for processing measurement and the test result from the test strip may be inaccurate.

In other embodiment in accordance with the present invention, the reaction area further comprises a second humidity test line (635), and the second humidity test line (635) also contains a humidity detecting material for detecting humidity variation with color change. The casing (70) further comprises an opening (76) corresponding to the second humidity test line (635). The casing (70) is designed for exposing the second humidity test line (635) to outer environment by the opening (76), and the humidity test line (634) is unexposed to outer environment. For example, there is designed a baffle between the humidity test line (634) and the second humidity test line (635), or the opening (76) is designed for positioning in the window (74) corresponding to one of the humidity test line (635) to let it expose to outer environment. The electronic analysis device is detecting color change of the humidity test line (634) and the second humidity test line (635) to obtain a first humidity detected value and a second humidity detected value, and calculating the ratio of the first humidity detected value and the second humidity detected value then comparing with a predetermined range to determine whether the test strip is appropriated for processing measurement or showing an error message.

The test strip further comprises a reagent area (62) between the sample introducing area (61) and the reaction area (63). The reagent area (62) contains a substrate to be reacting with the analyte and moving with the sample flow. The sample passes through the reagent area (62) and carries the reagent substrate to move toward the reaction area (63).

In a preferred embodiment in accordance with the present invention, the reaction area (63) further comprises a control line (633) and it indicates reliable reaction in the test strip when showed.

For example, when the test strip is used for pregnancy diagnosis, the reagent area (62) contains mouse anti-hCG α chain antibody with color tag, and the test line (632) contains anti-hCG β chain antibody and the control line (633) contains goat IgG antibody.

The present invention is not only related with the test strip and the method for humidity detection but also the method for detecting humidity to correct analyte concentration.

Figure 7:
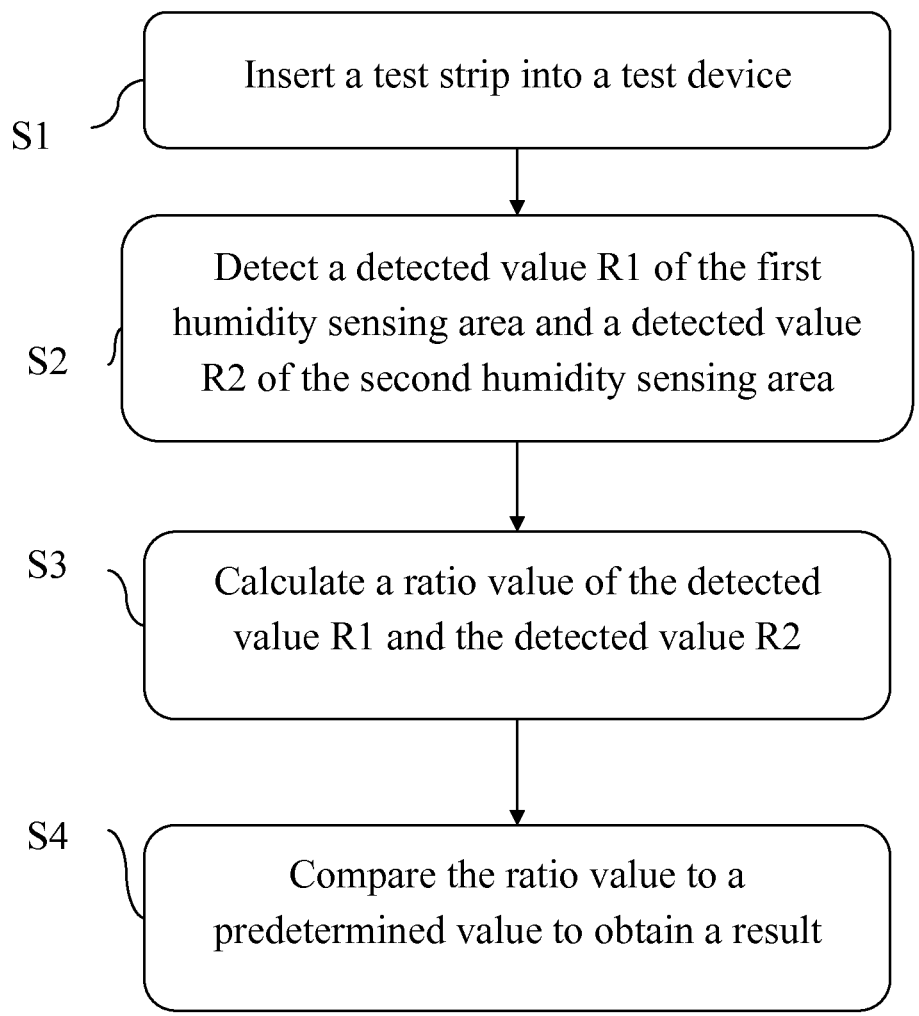
FIG. 7 is a flow chart of a preferred embodiment of a method of humidity detection in accordance with the present invention.

Please refer to FIG. 7, the present invention provides a method for humidity detection, comprising inserting a test strip into a test device (S1); detecting a detected value R1 of the first humidity sensing area and a detected value R2 of the second humidity sensing area on the test strip (S2), preferably, the detected value can be resistance value, capacitance value or inductance value; calculating a ratio value of the detected value R1 and the detected value R2 (S3); and comparing the ratio value to a predetermined value to obtain a result (S4). Comparing the ratio value of two detected values can prevent the deviation caused by detecting the absolute value of solo humidity sensing area.

Figure 8:
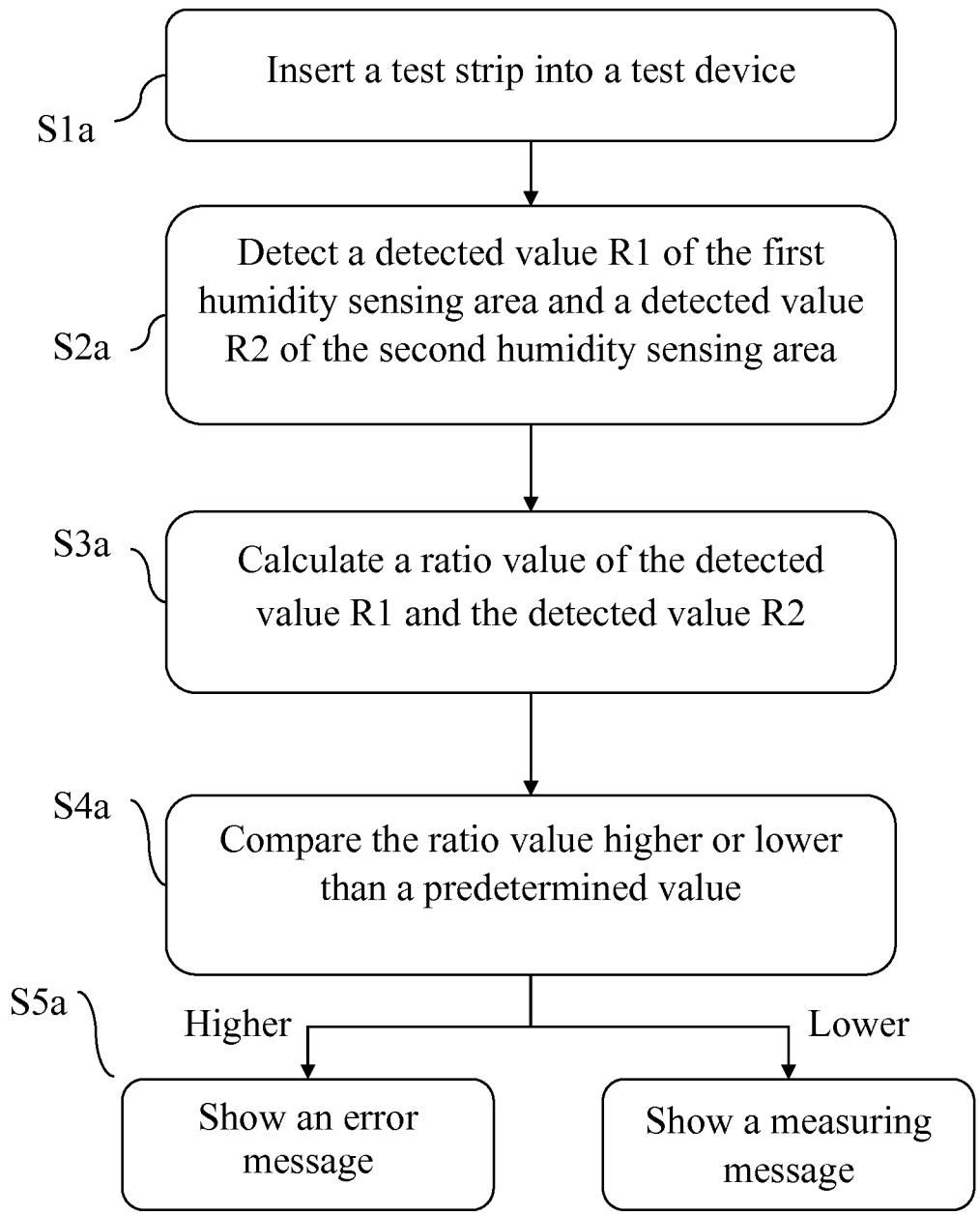
FIG. 8 is a flow chart of a preferred embodiment of a method of measuring analyte concentration in accordance with the present invention.

Please refer to FIG. 8, the present invention provides a method for measuring analyte concentration, comprising inserting a test strip into a test device (S1a); detecting a detected value R1 of the first humidity sensing area and a detected value R2 of the second humidity sensing area on the test strip (S2a), preferably, the detected value can be resistance value, capacitance value or inductance value; calculating a ratio value of the detected value R1 and the detected value R2 (S3a); comparing the ratio value to a predetermined value (S4a); if the ratio value higher than the predetermined value, then showing an error message (S5a); if the ratio value lower than the predetermined value, then showing a measuring message (S6a).

For example, please refer to FIG. 3A, the test strip contacted with the mating test device so that the contact pad is contacted with a connector of the test device for transmitting the electronic signal and the detected electronic signal from test device. The electronic signal can be current or voltage. There is a particular equation relationship between the resistant value and the current or the voltage so that detected the current or the voltage can export the resistant value. When detecting the resistant value of the first humidity sensing area (262) and the second humidity sensing area (264), there can obtain the first resistant value R1 between HW1 and HR and obtain the second resistant value R2 between HW2 and HR. Then obtain a ratio of the value R1 and R2 to compare with a predetermined value for determining the humidity condition of the test strip. When the ratio value higher than the predetermined value, the test device can show the error message, and therefore, users realize that the test strip is inappropriate for use that preventing inaccurate measurement result. When the ratio value lower than the predetermined value, the test device can show the measuring message to inform users processing measurement.

For example, if presumed the predetermined value is 0.8, it is indicated the condition of the test strip has been exceeding humidity range when the ratio value R1/R2 is higher than 0.8.

The predetermined value can be obtained from the humidity detection with each batch of test strip before sale and take input into the test device.

The present invention shall not be limited with the embodiment described above. The ratio value can be R1/R2 or R2/R1. When the ratio value is higher or lower than the predetermined value, it has an indication to inform users, such as twinkling/lighting indicative lamp, noising the alarm, voice speaking, displaying on the screen and so on.

Figure 9:
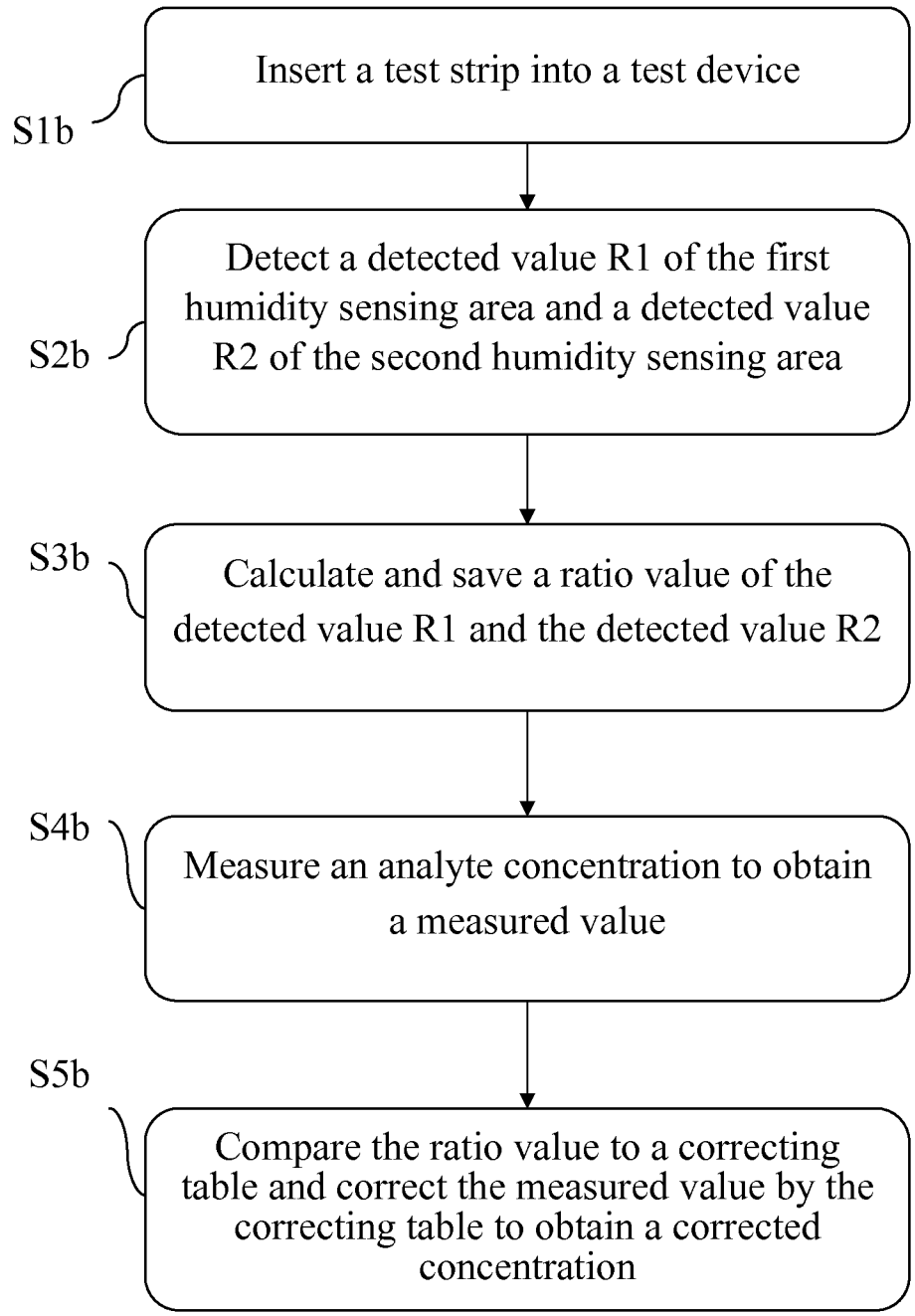
FIG. 9 is a flow chart of other preferred embodiment of a method of measuring analyte concentration in accordance with the present invention.

In other preferred embodiment, please refer to FIG. 9, the present invention provides a method for measuring analyte concentration, comprising inserting a test strip into a test device (S1b); detecting a detected value R1 of the first humidity sensing area and a detected value R2 of the second humidity sensing area on the test strip (S2b), preferably, the detected value can be resistance value, capacitance value or inductance value; calculating and saving a ratio value of the detected value R1 and the detected value R2 (S3b); measuring an analyte concentration to obtain a measured value (S4b); comparing the ratio value to a correcting table and correcting the measured value to obtain a corrected concentration (S5b).

For example, the ratio value R1/R2 is 0.7 so that the measured value is corresponding to the correcting table used for the ratio value 0.7, or the ratio value R1/R2 is 0.75 so that the measured value is corresponding to the correcting table used for the ratio value 0.75.

Accordingly, the present invention has advantages and characteristics listed as follows:

1. The test strip in accordance with the present invention for humidity detection by detecting and calculating the ratio value of resistant value or other detected value between two humidity sensing areas is reducing deviation from detecting solo humidity sensing area affected by manufacturing process, environment, temperature and so on.

2. The method for humidity detection in accordance with the present invention by comparing the ratio value from resistant value or other detected value between two humidity sensing areas to a predetermined value is reducing deviation from detecting solo humidity sensing area affected by the thickness of humidity sensing area from manufacturing, environment humidity and temperature in detection.

3. The method of measuring analyte concentration and the test strip in accordance with the present invention is used for humidity detection so as to determine if the humidity of test strip is over normal range to inform users whether the test strip is appropriated to process measurement.

4. The method of measuring analyte concentration in accordance with the present invention is correcting the measured value of analyte concentration to obtain a corrected concentration from humidity correcting.

More exemplary embodiments and advantages of the present invention may be ascertained by reviewing the present disclosure and the accompanying drawing. It is intended that the description and embodiments with reference to the accompanying drawing to be considered as exemplary only.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An test strip for humidity detection, comprising:
a base;
an electrode detecting element disposed on the base;
two humidity detecting materials respectively disposed on the electrode detecting element; and
a cover disposed upon the electrode detecting element and the base, and the cover letting one of the humidity detecting materials be exposed to the outer environment.

2. The test strip as claimed in claim 1, wherein the electrode detecting element has a humidity sensing trace near one end of the test strip, and the humidity sensing trace comprises a first humidity sensing area and a second humidity sensing area, and the two humidity detecting materials are respectively disposed on the first humidity sensing area and the second humidity sensing area.

3. The test strip as claimed in claim 2, wherein the electrode detecting element comprises at least one contact pad, at least one electrode and at least one conducting trace disposed between the contact pad and the electrode, and the contact pad and the electrode are disposed on different sides of the electrode detecting element, and the humidity detecting materials vary in their impedance values as the humidity changes.

4. The test strip as claimed in claim 3, wherein the first humidity sensing area and the second humidity sensing area respectively comprise two electrodes and two conducting traces, and the electrodes are respectively connected with different the contact pads.

5. The test strip as claimed in claim 4, wherein the first humidity sensing area and the second humidity sensing area are shared with one of the electrodes or the conducting traces.

6. The test strip as claimed in claim 4, wherein the electrode system consists of a silver layer and a carbon layer, and the electrode surface of the silver layer is larger than that of the carbon layer in the humidity sensing area.

7. The test strip as claimed in claim 3, wherein the contact pad is adapted to be contacted with a mating test device which is used for detecting an impedance value of the humidity sensing area.

8. The test strip as claimed in claim 2, wherein the humidity sensing trace is comb-shaped.

9. The test strip as claimed in claim 2, wherein one of the humidity sensing areas is disposed near a lateral edge of the base and the cover cooperates with the base to form a notch on the lateral edge corresponding to the one of the humidity sensing areas to let the one of the humidity sensing areas be exposed to the outer environment.

10. The test strip as claimed in claim 9, further comprising an isolating layer disposed between the cover and the electrode detecting element, and exposed at least one end of the electrode detecting element to form a space between the cover and the base; wherein the isolating layer comprises an opening notch corresponding to the lateral edge of one of the humidity sensing areas.

11. The test strip as claimed in claim 1, wherein the cover further comprises a hole, and the hole is located corresponding to one of the humidity detecting materials to let it be in an exposed state, and the other one of the humidity detecting materials is in an unexposed state.

12. The test strip as claimed in claim 1, wherein the test strip further comprises a reaction area used to react with an analyte in the sample for providing a measurement of a concentration of the analyte.

13. A test strip for humidity detection, comprising:
a reaction area comprising two humidity sensing traces, and the two humidity sensing traces respectively comprising a humidity detecting material; and
a casing covering the reaction area so as to let one of the humidity detecting materials be exposed to the outer environment.

14. The test strip as claimed in claim 13, wherein the casing further comprising an opening to let the one of the humidity detecting materials be exposed to the outer environment.

15. The test strip as claimed in claim 13, further comprising:
a sample introducing area used for receiving a sample;
the reaction area receiving the sample from the sample introducing area, and further comprising a test line used for combining with an analyte.

16. A method for humidity detection, comprising:
inserting a test strip into a test device, wherein the test strip comprising a first humidity sensing area and a second humidity sensing area;
detecting a value R1 of the first humidity sensing area and a value R2 of the second humidity sensing area;
calculating a ratio value of the value R1 and the value R2; and
comparing the ratio value to a predetermined value to obtain a result.

17. The method as claimed in claim 16, wherein the values R1 and R2 are resistance values, capacitance values or inductance values.

18. The method as claimed in claim 16, further comprising showing an error message or a measuring message when the ratio value is higher or lower than the predetermined value.

19. The method as claimed in claim 16, wherein one of the humidity sensing areas in the test strip is in an exposed state, and the other one of the humidity sensing areas is in an unexposed state.

20. The method as claimed in claim 16, after calculating the ratio value of the detected value R1 and the detected value R2 further comprising:
saving the ratio value;
measuring an analyte concentration to obtain a measured value;
comparing the ratio value to a correcting table; and
correcting the measured value by the correcting table to obtain a corrected concentration.

* * * * *